US012690940B2

(12) United States Patent
Levy et al.

(10) Patent No.: US 12,690,940 B2
(45) Date of Patent: ***Jul. 28, 2026

(54) SURGICAL CLEANING TOOL, SYSTEMS, AND METHODS

(71) Applicant: Mazor Robotics Ltd., Caesarea (IL)

(72) Inventors: Arik Levy, Herzliya (IL); Eli Zehavi, Haifa (IL)

(73) Assignee: Mazor Robotics Ltd., Caesarea (IL)

( * ) Notice: Subject to any disclaimer, the term of this patent is extended or adjusted under 35 U.S.C. 154(b) by 356 days.

This patent is subject to a terminal disclaimer.

(21) Appl. No.: 18/371,914

(22) Filed: Sep. 22, 2023

(65) Prior Publication Data

US 2024/0008953 A1     Jan. 11, 2024

Related U.S. Application Data

(63) Continuation of application No. 16/984,490, filed on Aug. 4, 2020, now Pat. No. 11,793,599.

(51) Int. Cl.
    B08B 9/04     (2006.01)
    A61B 90/70    (2016.01)
        (Continued)

(52) U.S. Cl.
    CPC .............. *A61B 90/70* (2016.02); *A61F 13/05* (2024.01); *B08B 9/045* (2013.01); *B08B 9/047* (2013.01); *B08B 9/057* (2013.01); *A61B 34/30* (2016.02); *A61B 2217/005* (2013.01); *A61B 2217/007* (2013.01); *A61M 1/88* (2021.05); *A61M 1/90* (2021.05)

(58) Field of Classification Search
    CPC ........... B08B 9/04; B08B 9/047; A61B 90/70; A61B 34/30
    See application file for complete search history.

(56) References Cited

U.S. PATENT DOCUMENTS

| | | | |
|---|---|---|---|
| 6,391,034 | B1 | 5/2002 | Adamson et al. |
| 6,440,138 | B1 | 8/2002 | Reiley et al. |
| | (Continued) | | |

FOREIGN PATENT DOCUMENTS

| | | |
|---|---|---|
| CN | 204499822 | 7/2015 |
| CN | 205379006 | 7/2016 |
| | (Continued) | |

OTHER PUBLICATIONS

Official Action with English Translation for China Patent Application No. 202180058675.X, dated Jan. 22, 2026, 18 pages.

(Continued)

*Primary Examiner* — Michael D Jennings
(74) *Attorney, Agent, or Firm* — Sheridan Ross P.C.

(57) ABSTRACT

A surgical tool, systems, and method for cleaning an anatomical space is provided. At least one brush is disposed on a shaft extending through a tube. The tube includes a corresponding brush slot for each brush. A motor is operable to rotate the shaft to cause the at least one brush to move from a closed position to a cleaning position. The at least one brush is positioned entirely inside of the tube when in the closed position and at least partially outside of the tube when in the cleaning position. A fluid source is operable to supply fluid to the at least one brush as the at least one brush passes through the brush slot.

20 Claims, 6 Drawing Sheets

(51) Int. Cl.

| | | |
|---|---|---|
| *A61F 13/05* | (2024.01) |
| *B08B 9/045* | (2006.01) |
| *B08B 9/047* | (2006.01) |
| *B08B 9/057* | (2006.01) |
| *A61B 34/30* | (2016.01) |
| *A61M 1/00* | (2006.01) |

(56) References Cited

U.S. PATENT DOCUMENTS

| | | | |
|---|---|---|---|
| 7,520,886 B2 | 4/2009 | Surti | |
| 7,637,927 B2 | 12/2009 | Hyde, Jr. | |
| 8,118,813 B2 | 2/2012 | Perez-Cruet et al. | |
| 8,273,088 B2 | 9/2012 | Zalenski et al. | |
| 9,161,773 B2 | 10/2015 | Schaller et al. | |
| 9,226,792 B2 | 1/2016 | Bloom | |
| 9,345,488 B2 | 5/2016 | Assell et al. | |
| 10,537,340 B2 | 1/2020 | Mirochinik et al. | |
| 10,786,072 B1 * | 9/2020 | Robinson | A46B 9/10 |
| 10,900,211 B1 * | 1/2021 | Lei | B08B 9/045 |
| 11,793,599 B2 * | 10/2023 | Levy | A46B 9/10 |
| 2003/0109837 A1 | 6/2003 | Mcbride-Sakal | |
| 2006/0264957 A1 | 11/2006 | Cragg et al. | |
| 2007/0021752 A1 * | 1/2007 | Rogers | A61B 17/162 |
| | | | 606/80 |
| 2007/0149990 A1 | 6/2007 | Palmer et al. | |
| 2007/0198020 A1 * | 8/2007 | Reiley | A61B 17/320016 |
| | | | 606/79 |
| 2007/0213584 A1 | 9/2007 | Kim et al. | |
| 2008/0208230 A1 | 8/2008 | Chin et al. | |
| 2010/0030216 A1 | 2/2010 | Arcenio | |
| 2011/0154596 A1 | 6/2011 | Madan | |
| 2011/0184447 A1 | 7/2011 | Leibowitz et al. | |
| 2011/0319941 A1 | 12/2011 | Bar et al. | |
| 2013/0035691 A1 | 2/2013 | Boylan et al. | |
| 2013/0317529 A1 | 11/2013 | Golden et al. | |
| 2016/0235418 A1 | 8/2016 | Mimran | |
| 2016/0302813 A1 | 10/2016 | Butterfield | |
| 2018/0119406 A1 * | 5/2018 | Scott | E03F 9/005 |
| 2018/0142458 A1 * | 5/2018 | Bowles | E03F 9/005 |
| 2018/0249903 A1 | 9/2018 | Strombergsson et al. | |
| 2018/0289432 A1 | 10/2018 | Kostrzewski et al. | |
| 2018/0296285 A1 | 10/2018 | Simi et al. | |
| 2019/0328599 A1 | 10/2019 | Mahoney | |
| 2020/0205645 A1 | 7/2020 | Hashimoto et al. | |
| 2020/0205908 A1 | 7/2020 | Julian et al. | |
| 2020/0291632 A1 * | 9/2020 | Scott | E03F 9/005 |

FOREIGN PATENT DOCUMENTS

| | | | | |
|---|---|---|---|---|
| CN | 107812264 | 3/2018 | | |
| CN | 108430351 | 8/2018 | | |
| JP | 2001-054522 | 2/2001 | | |
| WO | WO 2010/121206 | 10/2010 | | |
| WO | WO 2011/149926 | 12/2011 | | |
| WO | WO-2011149926 A1 * | 12/2011 | | A61B 17/50 |

OTHER PUBLICATIONS

International Search Report and Written Opinion for International (PCT) Patent Application No. PCT/IL2021/050931, dated Nov. 23, 2021, 18 pages.

Official Action for U.S. Appl. No. 16/984,490, dated Jul. 27, 2022, 25 pages.

Official Action for U.S. Appl. No. 16/984,490, dated Nov. 21, 2022, 22 pages.

Notice of Allowance for U.S. Appl. No. 16/984,490, dated Jun. 14, 2023, 9 pages.

* cited by examiner

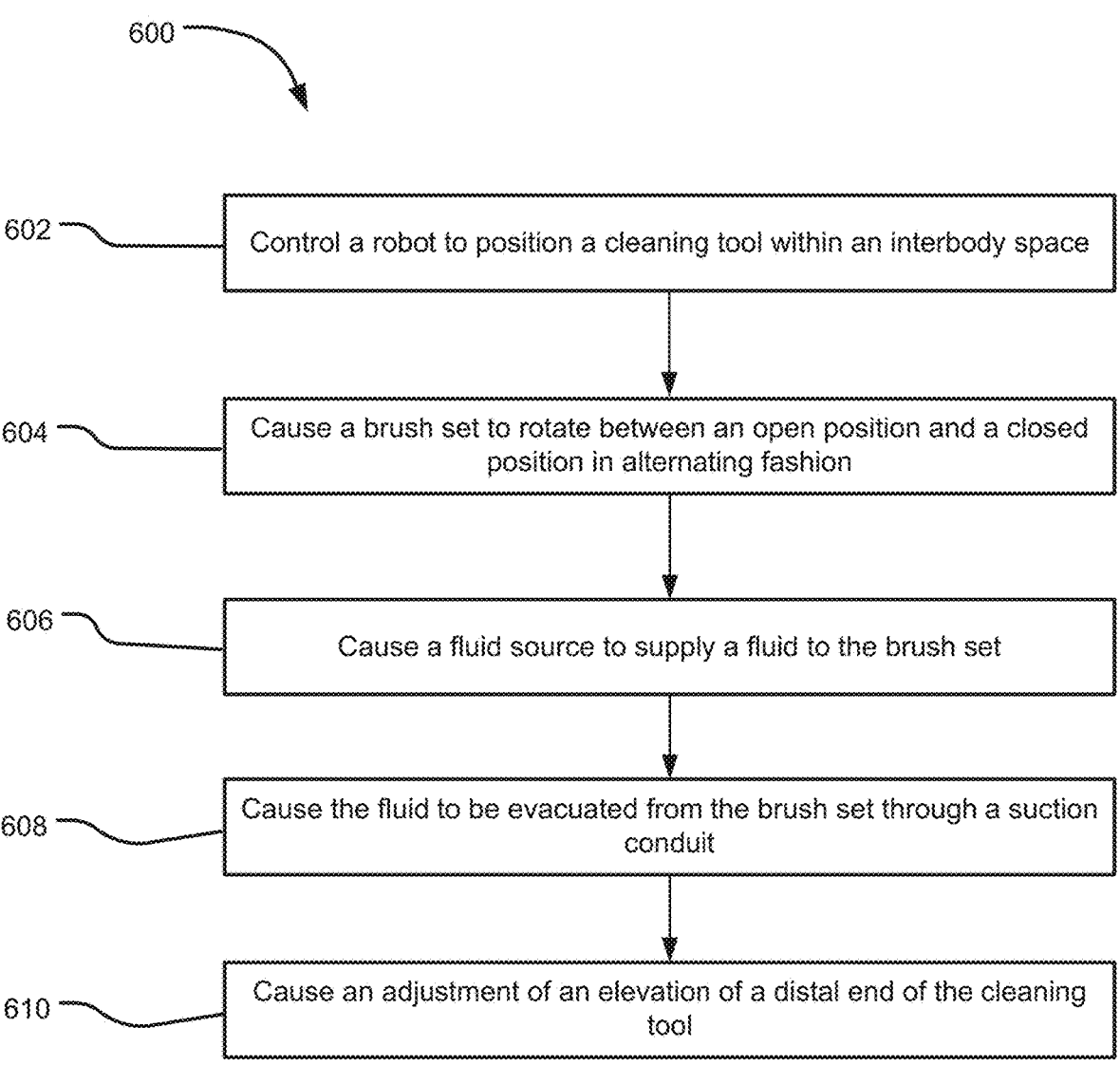

600

602 — Control a robot to position a cleaning tool within an interbody space

604 — Cause a brush set to rotate between an open position and a closed position in alternating fashion 606 — Cause a fluid source to supply a fluid to the brush set 608 — Cause the fluid to be evacuated from the brush set through a suction conduit 610 — Cause an adjustment of an elevation of a distal end of the cleaning tool

FIG. 6

SURGICAL CLEANING TOOL, SYSTEMS, AND METHODS

CROSS REFERENCE TO RELATED APPLICATIONS

This application is a continuation of U.S. patent application Ser. No. 16/984,490, filed on Aug. 4, 2020, and entitled "Surgical Cleaning Tool, Systems, and Methods," the entire disclosure of which is incorporated herein by reference in its entirety.

FIELD

The present technology is generally related to surgical tools, and is more specifically related to tools for anatomical surface preparation.

BACKGROUND

During a surgical procedure, and in particular during a spinal interbody fusion, surgical cleaning tools, such as brushes, may be used to prepare a surface of an anatomical element for the procedure or for a particular step thereof. A surgical robot may be used to assist with or autonomously carry out one or more steps of a surgical procedure.

SUMMARY

Exemplary aspects of the present disclosure include:

A surgical tool according to at least one embodiment of the present disclosure comprises: at least one brush disposed on a shaft extending through a tube, the tube having a corresponding brush slot for each brush; a motor operable to rotate the shaft to cause the at least one brush to move from a closed position to a cleaning position, the at least one brush positioned entirely inside of the tube when in the closed position and at least partially outside of the tube when in the cleaning position; and a fluid source operable to supply fluid to the at least one brush as the at least one brush passes through the brush slot.

Any of the aspects herein, wherein the fluid is supplied through a conduit of the shaft.

Any of the aspects herein, wherein the at least one brush defines a substantially circular shape having a brush axis parallel to and offset from a shaft axis of the shaft, and rotation of the shaft causes the at least one brush axis to orbit around the shaft axis.

Any of the aspects herein, wherein the tube comprises a first conduit parallel to a second conduit, and wherein each of the at least one brush axis and the shaft axis are parallel to and offset from an axis of the second conduit.

Any of the aspects herein, further comprising a suction conduit for evacuating the fluid.

Any of the aspects herein, further comprising at least one evacuation slot disposed near the at least one brush slot, the at least one evacuation slot in communication with the suction conduit.

Any of the aspects herein, wherein as the at least one brush passes through the corresponding brush slot from the cleaning position to the closed position, the fluid and the corresponding evacuation slot evacuate the fluid from the at least one brush.

Any of the aspects herein, wherein the at least one brush comprises a plurality of steel bristles of varying lengths.

Any of the aspects herein, wherein the plurality of steel bristles forms a circle.

Any of the aspects herein, wherein the at least one brush comprises three brushes.

Any of the aspects herein, further comprising an elevation motor configured to vertically move the tool during operation of the tool.

A method for brushing an anatomical element according to at least one embodiment of the present disclosure comprises: causing at least one brush of the surgical tool to alternately rotate between a cleaning position and a closed position, the at least one brush positioned entirely within a perimeter of a tube of the surgical tool when in the closed position, the tube having a corresponding slot for each brush; causing a fluid source of the surgical tool to supply a fluid to the at least one brush from a fluid source as the at least one brush rotates through the closed position; and evacuating the fluid from the at least one brush through a suction conduit of the surgical tool, the suction conduit in fluid communication with an evacuation slot disposed near the slot.

Any of the aspects herein, wherein the brush is disposed on a shaft extending through the tube, the shaft comprising a bore and at least one fluid aperture positioned near the at least one brush, the fluid supplied to the at least one brush through the bore and the at least one fluid aperture.

Any of the aspects herein, further comprising: vertically moving the tool using a motor during operation of the tool.

Any of the aspects herein, wherein the at least one brush comprises a plurality of steel bristles of varying lengths.

A system for cleaning an anatomical space, according to at least one embodiment of the present disclosure comprises: at least one surgical tool comprising at least one brush, a corresponding slot for each brush, and a fluid source; a processor; and a memory storing instructions for execution by the processor that, when executed, cause the processor to: cause the at least one brush of the surgical tool to rotate between a cleaning position and a closed position, the at least one brush contacting the anatomical element when in the cleaning position; cause the fluid source to supply a fluid to the at least one brush, wherein as the at least one brush passes through the corresponding brush slot from the cleaning position to the closed position, the fluid and the corresponding brush slot evacuate loose anatomical elements from the at least one brush; and evacuate the fluid and the loose anatomical elements from the at least one brush.

Any of the aspects herein, wherein the at least one brush comprises a plurality of steel bristles of varying lengths.

Any of the aspects herein, wherein the instructions for execution by the processor, when executed, further cause the processor to cause a motor to vertically move the tool during operation of the tool.

Any of the aspects herein, wherein the surgical tool comprises a shaft, the at least one brush disposed on the shaft.

Any of the aspects herein, wherein the at least one brush defines a substantially circular shape having a brush axis parallel to and offset from a shaft axis of the shaft, rotation of the shaft causes the at least one brush axis to orbit around the shaft axis.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

4

Figure 1B:
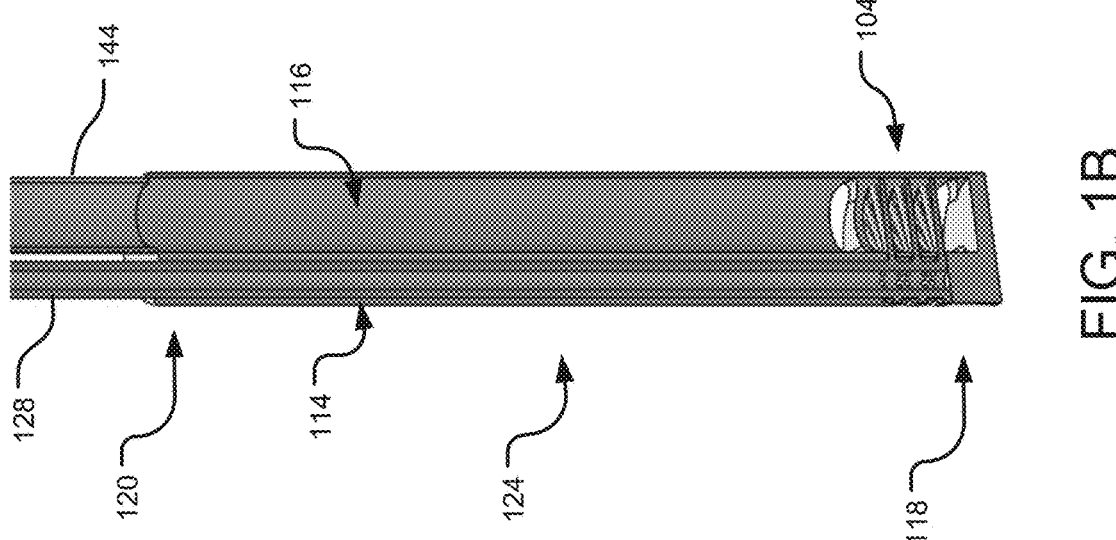
FIG. 1B depicts a close-up view of a distal portion of the tool of FIG. 1A according to at least one embodiment of the present disclosure.
Figure 1A:
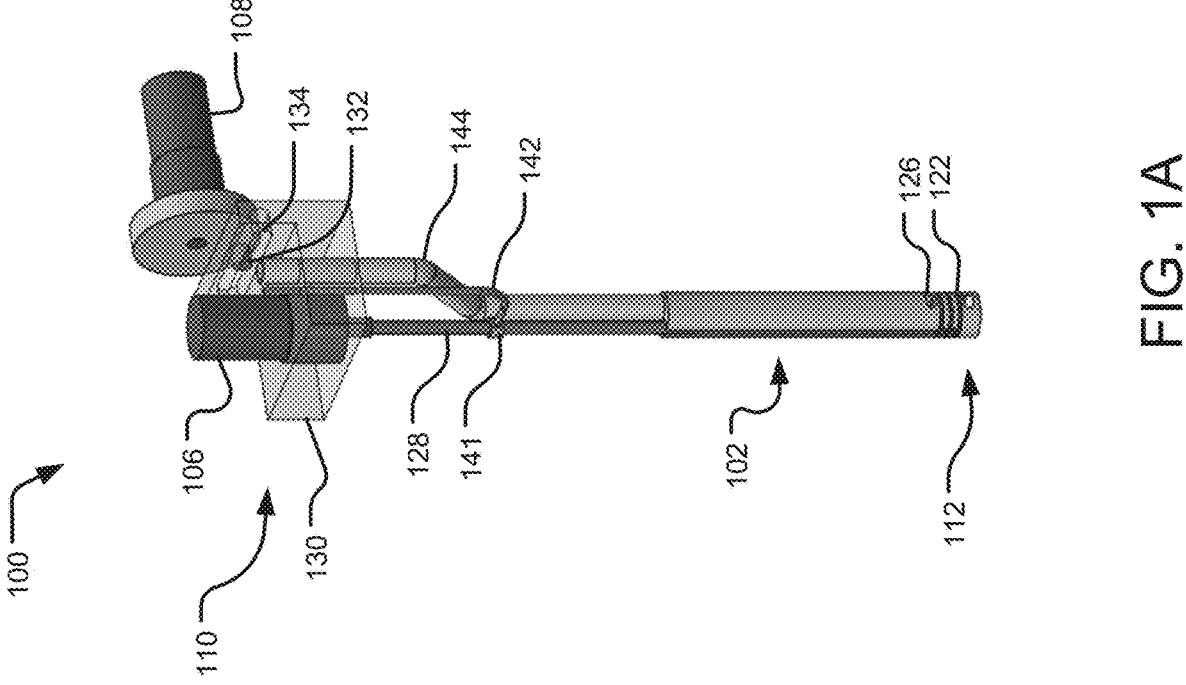
FIG. 1A depicts a surgical cleaning tool according to at least one embodiment of the present disclosure.
Figures 4A, 4B, 4C, 4D, 4E, 4F:
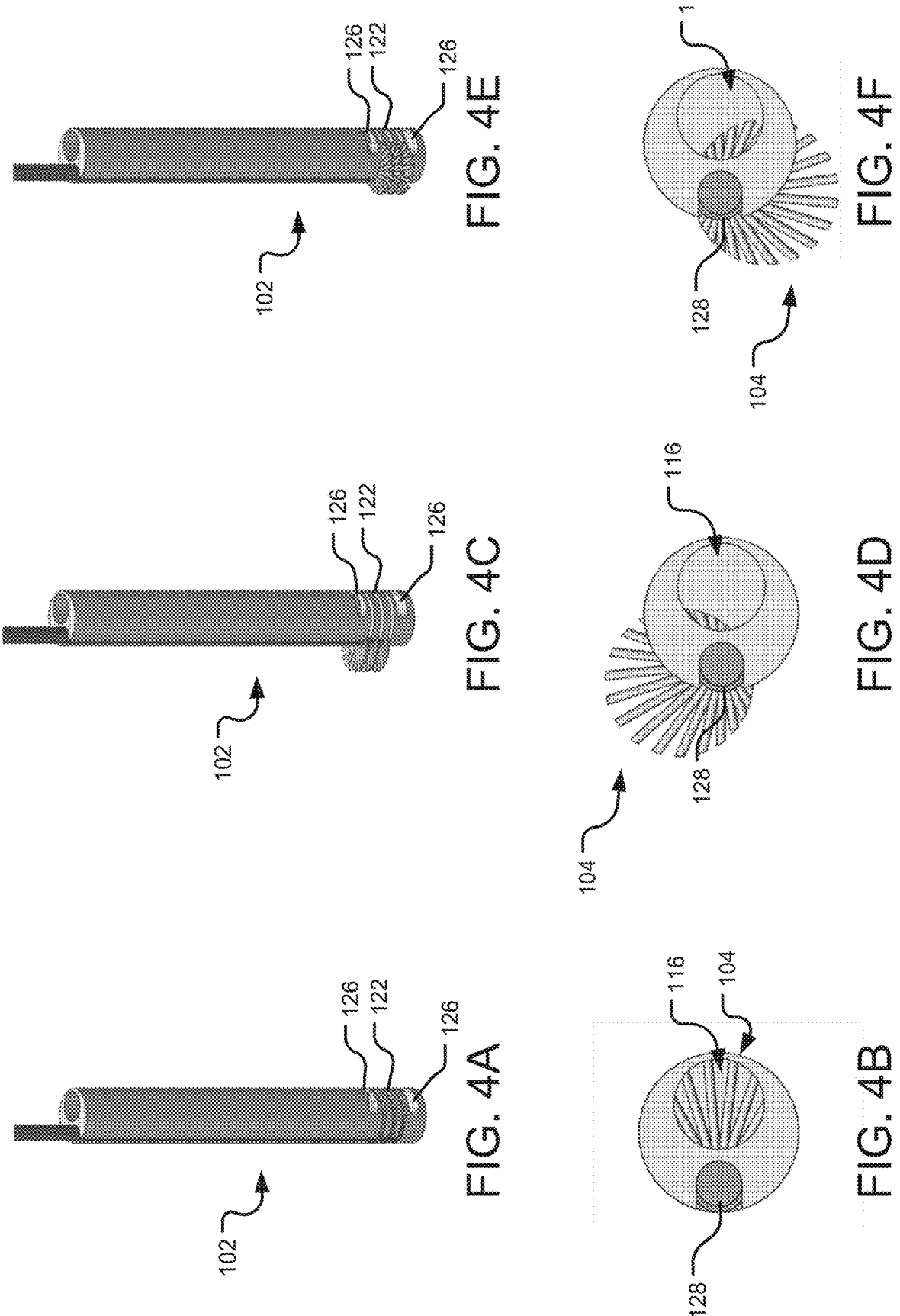
Figure 5:
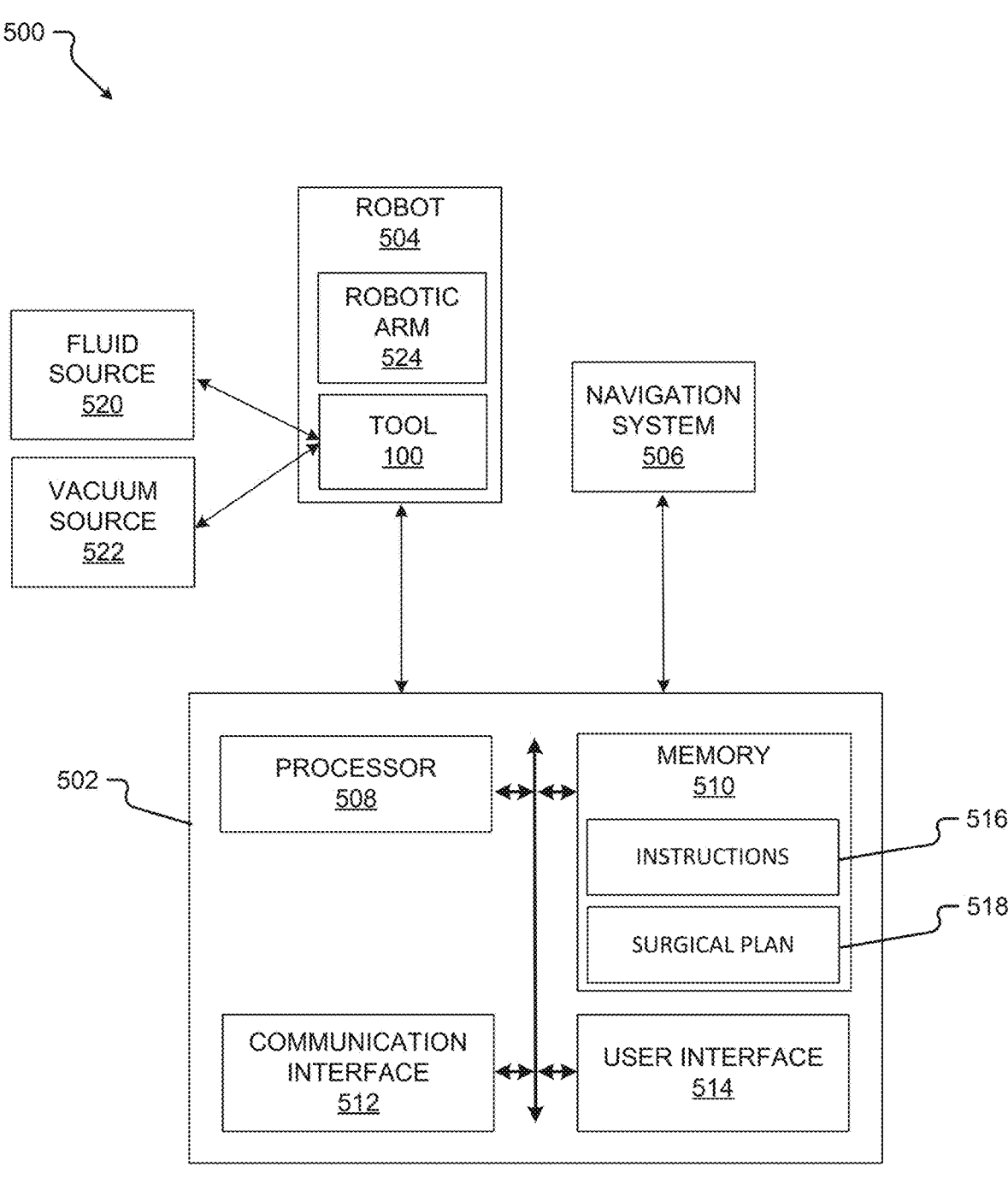

FIG. 4A depicts a perspective view of a portion of the tool of FIG. 1A in a first configuration, according to at least one embodiment of the present disclosure;

FIG. 4B depicts a top view of a portion of the tool of FIG. 1A in the first configuration, according to at least one embodiment of the present disclosure;

FIG. 4C depicts a perspective view of a portion of the tool of FIG. 1A in a second configuration, according to at least one embodiment of the present disclosure;

FIG. 4D depicts a top view of a portion of the tool of FIG. 1A in the second configuration, according to at least one embodiment of the present disclosure;

FIG. 4E depicts a perspective view of a portion of the tool of FIG. 1A in a third configuration, according to at least one embodiment of the present disclosure;

FIG. 4F depicts a top view of a portion of the tool of FIG. 1A in the third configuration, according to at least one embodiment of the present disclosure;

FIG. 5 is a block diagram of a system according to at least one embodiment of the present disclosure; and FIG. 6 is a flowchart of a method according to at least one embodiment of the present disclosure.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the methods of this disclosure may be performed by a combination of units or modules associated with, for example, a computing device and/or a medical device (including a medical imaging device).

In one or more examples, one or more steps of the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure. Similarly, the term "exemplary" as used herein means "example." Also, unless explicitly stated otherwise, terms such as "about" and "approximately" when used in connection with a stated value mean within ten percent of the stated value.

Disc removal is a critical step in spinal interbody fusion. Some of the challenges of disc removal include that disc removal currently takes significant time and is often incomplete (e.g., the interbody space is not thoroughly cleaned of all disc remnants), leading to a risk of non-fusion. The nucleus pulposus, or inner core of the vertebral disc, is a sticky material not easily removed. Forceps can be used for some bulk reduction (e.g., removal of larger segments of the disc), but cannot clean the end plates sufficiently. Brushes are often used for end plate preparation, but each can be used only a single time, as cleaning the brushes (e.g., to remove the sticky nucleus pulposus material from the brush's bristles) is impractical. Thus, use of multiple brushes may be required for disc removal. With forceps and/or brushes, the removal and cleaning process is lengthy and incomplete. Moreover, many in-out maneuvers are required, endangering neutral tissue. Attempted mechanical solutions for disc removal have failed, at least in part due to an inability to overcome such problems as the stickiness of the material being removed, clogging suction tubes, and smoothing burring surfaces.

The solution described herein comprises a rotating brush to remove disc material, coupled with an integrated cleaning mechanism. The eccentric brush at its closed configuration is in the form of a tube, so as to allow a clean entry to the disc. The eccentric brush spins and cleans the end plate, then goes through a thin slot in the cleaning tool that wipes the brush and, by doing so, cleans the brush at every single spin. In order to remove solid matter dislodged from the end plate and from the brush, the cleaning tool includes an irrigation and vacuum system.

Embodiments of the present disclosure may be particularly useful, for example, during surface preparation in connection with spinal interbody fusion.

Inclusion of a slot, irrigation system, and vacuum system increases the life of a brush and reduces the need to use multiple brushes for one procedure, while also reducing and/or eliminated time associated with changing brushes and reducing or eliminating multiple entries and exits of cleaning tools to the surgical site, thus better protecting neutral tissue from unnecessary damage. The brush may also be sterilized and is thus reusable.

Embodiments of the present disclosure also provide a brush housed in a tube during positioning of the brush for cleaning, thereby protecting the brush (as well as neutral tissue along the insertion path) from damage. Tools according to embodiments of the present disclosure are also advantageously small and non-intrusive, and may be suitable for minimally invasive procedures.

As described more fully below, a cleaning tool according to at least some embodiments of the present disclosure may be designed to clean an anatomical element with a brush that moves between a cleaning position and a closed position, a fluid supply that supplies fluid to the brush to clean the brush, and an evacuation conduit for evacuating the fluid and loose anatomical particles from the anatomical element and/or the volume in proximity thereto.

With reference first to FIGS. 1A and 1B, a cleaning tool 100 according to at least one embodiment of the present disclosure comprises a tube 102, a brush set 104, a brush motor 106, an elevation motor 108, a fluid source 520 (shown in FIG. 5), and a vacuum source 522 (shown in FIG. 5). In some embodiments, the tool 100 may have fewer components or more components. For example, the tool 100 may not include the elevation motor 108, the fluid source 520, and/or the vacuum source 522 (shown in FIG. 5). The tool 100 may be used to prepare a surface of an anatomical element (which may be, for example, a vertebral endplate) using a single, reusable brush or brush set. The tool 100 includes a proximal portion 110 opposite a distal portion 112. The tool 100 may be held by a robot 504, as described with respect to FIG. 5, by a passive tool holder, or by a surgeon or other human, and may automatically (e.g., under control of the robot 504) or manually (e.g., under control of a surgeon) perform each step described herein.

In the illustrated embodiment, the tool 100 includes the tube 102. The tube 102 includes a first conduit 114 with a first axis parallel to a second axis of a second conduit 116, and also includes a first end 118 opposite a second end 120. The first conduit 114 may have a diameter less than, greater than, or equal to a diameter of the second conduit 116. The tube 102 may be any solid material including, but not limited to, metal, steel, plastic, or the like, or any combination thereof, and may be biocompatible. In some embodiments the tube 102 may have a diameter shaped for minimally invasive procedures for insertion into small incisions. For example, the diameter of the tube 102 may be 8 mm, though in other examples the tube 102 may have a diameter less than or greater than 8 mm. In other embodiments, the tube 102 may have a larger diameter.

The brush set 104 can include one brush, two brushes, or more than two brushes. The tube 102 may include a brush slot set 122. The brush slot set 122 may include one slot, two slots, or more than two slots, with the number of slots corresponding to the number of brushes in the brush set 104. In the illustrated embodiment, the brush slot set 122 comprises three slots positioned near the first end 118. In other embodiments, the brush slot set 122 may be positioned anywhere on the tube 102, for example, at or near the second end 120 or near a midportion 124 of the tube 102, depending on the particular anatomy being cleaned and from which anatomical particles are being evacuated. In the illustrated embodiment, each slot of the brush slot set 122 has a height substantially similar to or slightly larger than a height of each brush of the brush set 104 such that loose anatomical particles that may be stuck on each brush of the brush set 104 are dislodged by contact with the edges of the corresponding slot of the brush slot set 122. In other embodiments, each slot of the brush slot set 122 may have a height larger than the corresponding brush of the brush set 104.

The tube 102 may also include one or more evacuation slots 126. In the illustrated example, the tube 102 includes a first evacuation slot disposed above the brush slot set 122 and a second evacuation slot disposed below the brush slot set 122. In other embodiments, the tube 102 may include one evacuation slot or more than two evacuation slots. In further embodiments, the one or more evacuation slots may be disposed anywhere on the tube 102, for example, at or near the second end 120 or near the midportion 124 of the tube 102, depending on the particular anatomy being cleaned and from which anatomical particles are being evacuated. In the illustrated embodiment, the one or more evacuation slots 126 extend partially around a circumference of the tube 102 and have a height greater than the height of a slot of the brush slot set 122. In other examples, the one or more evacuation slots 126 may fully extend around the circumference of the tube and/or may have a height greater than or less than the height of a slot of the brush slot set 122. The one or more evacuation slots 126 may be sized to facilitate entry therethrough of anatomical particles dislodged by the brush set 104 during operation of the cleaning tool 100, and may further be sized to reduce a likelihood of being clogged by a plurality of anatomical particles being pulled into the second conduit 116 at once.

The brush motor 106 is disposed near the proximal portion 110 and is operable to rotate a shaft 128 to cause the brush set 104 to rotate from a closed position to a cleaning position and back to the closed position. The closed position is the position in which the greatest portion of the brush set 104 is enclosed within a perimeter of the tube 102, while the cleaning position is any rotational position of the brush set 104 other than in the closed position. In other words, the cleaning position encompasses any angular offset of the brush set 104 from the closed position (e.g., between 1 and 359 degrees offset from the closed position). In embodiments where the brush set 104 is entirely contained within a perimeter of the tube 102 when the brush set 104 is in the closed position, the cleaning position encompasses any position of the brush set 104 in which any portion of the brush set 104 extends beyond a perimeter of the tube 102.

The brush motor 106 in the illustrated embodiment is positioned on a motor bracket 130 and coupled to the shaft 128. The elevation motor 108 is also disposed near the proximal portion 110 and is configured to vertically move the tool 100 before, during, or after operation of the tool 100. In the illustrated embodiment, an elevation cam 132 extends through a cam slot 134 in the motor bracket 130 and slides along the cam slot 134 when the elevation motor 108 rotates. The cam 132 and the cam slot 134 translate the rotational movement of the elevation motor 108 to a translational movement (e.g., vertical) of the tool 100. Operation of the elevation motor 108 during operation of the cleaning tool 100 beneficially enables the brush set 104 to clean an entirety (or at least a significant portion) of an interbody disc space, despite having a substantially planar profile.

The brush motor 106 and the elevation motor 108 may be of the same or a different motor type than each other. In some embodiments, one or more gears, gear boxes, clutches, transmissions, and/or other mechanical elements may be utilized to enable a single motor to be used both to spin the shaft 128 and thus the brush set 104, and to adjust the elevation of the tool 100. The brush motor 106 and/or the elevation motor 108 may be an electric motor, a pneumatic motor, a hydraulic motor, or another type of motor. In some embodiments, the brush motor 106 and the elevation motor 108 each comprise a gear motor. In other embodiments, each of the brush motor 106 and the elevation motor 108 comprise any type of motor including, but not limited to, an AC brushless motor, a DC brushed motor, a DC brushless motor, a servo motor, or the like.

Figures 2A, 2B, 2C:
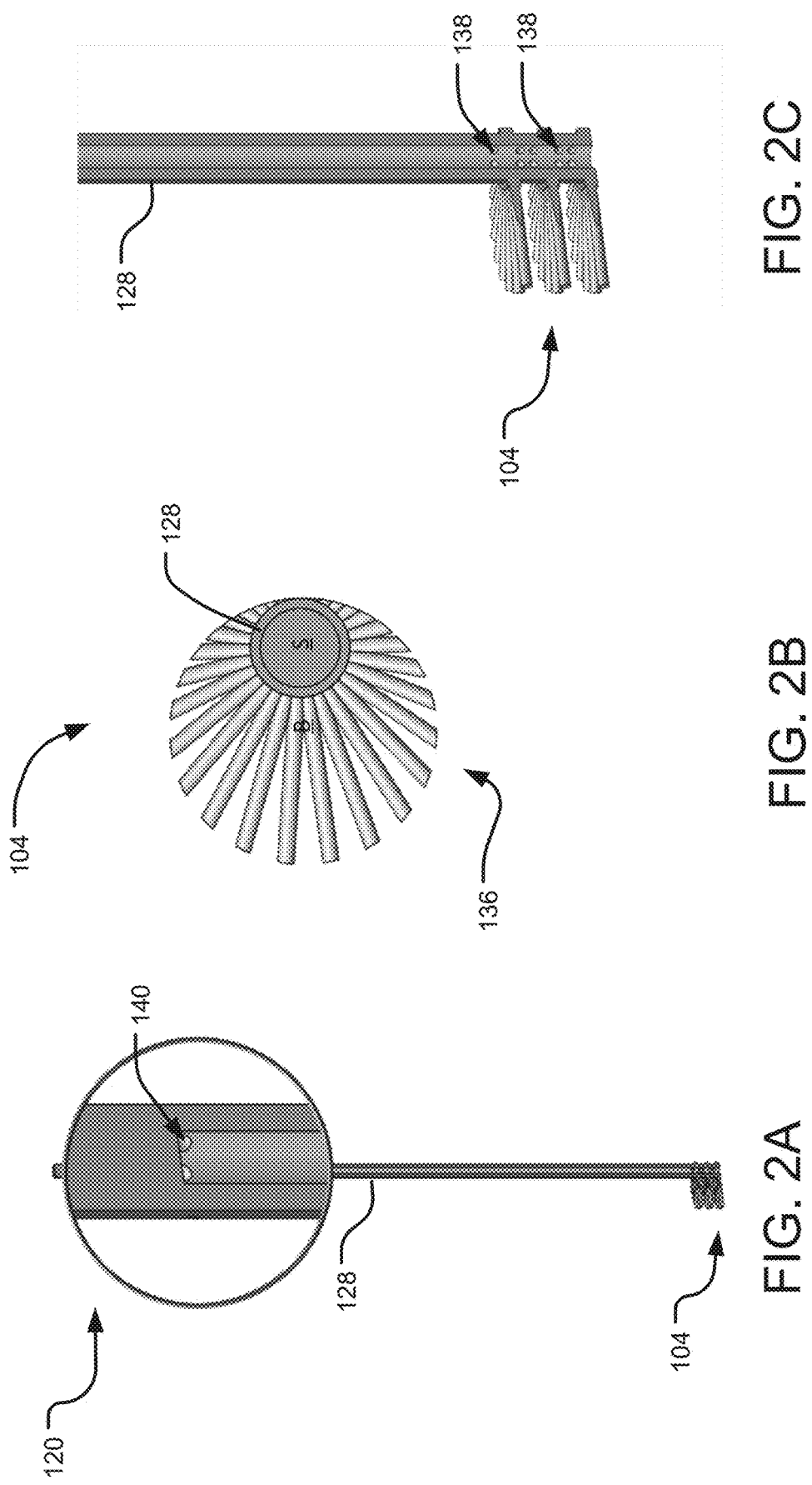
FIG. 2A depicts a perspective view of portion of the tool of FIG. 1A according to at least one embodiment of the present disclosure.
FIG. 2B depicts a close-up bottom view of the portion of the tool of FIG. 2A according to at least one embodiment of the present disclosure.
FIG. 2C depicts a close-up view of a distal portion of the portion of the tool of FIG. 2A according to at least one embodiment of the present disclosure.

FIGS. 2A-2C illustrate the brush set 104 in detail. The brush set 104 is positioned on the shaft 128 near the distal portion 112. The shaft 128 extends through the first conduit 114 of the tube 102 and has a shaft axis S parallel to (and, in some embodiments, coaxial with) the first conduit axis. The brush set 104 has a brush axis B at a center of the brush set 104 that is parallel to and offset from the shaft axis S and the first conduit axis, as shown in FIG. 2B. The brush axis B is parallel to the second conduit axis of the second conduit 116. Rotation of the shaft 128 causes the at least one brush axis B to orbit around the shaft axis S, thereby causing eccentric rotation of the brush set 104.

The brush set 104 and the shaft 128 may be a single piece (e.g., may be integrally formed), or separate pieces. In embodiments where the brush set 104 is separate from the shaft 128, the brush set 104 as a whole or the individual brushes thereof may be removable from the shaft 128 for replacement and/or cleaning. In other embodiments, the brush set 104 is fixed to the shaft 128 and the shaft 128 is removable from the tool 100 for cleaning and/or replacement. In further embodiments, the brush set 104 may be fixed to a portion of the shaft 128, and the portion may be removeable from the shaft 128 for cleaning and/or replacement.

In the illustrated example, the brush set 104 comprises three brushes spaced apart from each other. In other examples, the brush set 104 comprises one brush, two brushes, or more than three brushes. In examples where the brush set 104 comprises two or more brushes, each brush may be spaced from or adjacent to another brush. The brush set 104 may have a height substantially similar to a height of a spinal disc, though the brush set 104 may have a height less than or greater than a height of a spinal disc In some embodiments, the brush set 104 comprises a plurality of steel bristles of varying length. In other embodiments, the brush set 104 may comprise bristles of any type of material including, but not limited to, plastic, metal, synthetic fibers, natural fibers, or the like. As shown in FIG. 2B, the brush set 104 defines a substantially circular shape when viewed from the top or bottom. More specifically, the plurality of bristles form a circle. In other embodiments, the brush set 104 may define any shape including, but not limited to, a square, a triangle, an oval, a rectangle, a star, or the like. In such embodiments, the tube 102 may be provided with the same or a similar shape, so that the brush set 104 may rotate into a closed position in which the brush set 104 fits within an outer perimeter of the tube 102.

As previously described, the brush set 104 is movable from a closed position to a cleaning position. When the brush set 104 is in the closed position, the brush set 104 is positioned entirely inside of the tube 102, as shown in FIG. 4A. When the brush set 104 is in the cleaning position (or in any position other than the closed position), the brush set 104 is at least partially outside of the tube 102. During use, when each brush of the brush set 104 passes through the corresponding brush slot of the brush slot set 122 while rotating into or through the closed position, the fluid (from the fluid source 520, if used) and the corresponding brush slot of the brush slot set 122 facilitate dislodgment and evacuation of loose anatomical particles and/or fluid from each brush of the brush set 104 as well as the interbody space into which the distal portion 112 extends.

The fluid is supplied from the fluid source 520 through a conduit of the shaft 128. As shown in FIGS. 2A and 2C, the fluid enters the shaft 128 through one or more first fluid apertures 140 proximate the proximate portion 110 and exits the shaft 128 through one or more second fluid apertures 138 proximate the distal portion 112. In the illustrated embodiment, the one or more first fluid apertures 140 comprise a plurality of first fluid apertures positioned at or proximate a top end or top end portion of the shaft 128. In other embodiments, the one or more first fluid apertures 140 comprise a single aperture. The one or more first fluid apertures may be positioned anywhere on the shaft 128, although positioning the one or more first fluid apertures closer to the proximate portion 110 may facilitate the provision of fluid thereto from a fluid source 520.

The one or more second fluid apertures 138, as shown in the illustrated example, comprise a plurality of second fluid apertures positioned at a bottom end or bottom end portion of the shaft 128 and adjacent to the brush set 104. In the illustrated embodiment, the shaft 128 comprises a first set of second fluid apertures 138 positioned on a proximate side of each brush of the brush set 104, and a second set of a second fluid apertures 138 positioned on a distal side of each brush of the brush set 104. Such positioning of the second fluid apertures 138 beneficially enables fluid to be sprayed or otherwise discharged onto both sides of each brush of the brush set 104. In other embodiments, however, the second fluid apertures 138 may be positioned only on a proximate side of each brush, or only on a distal side of each brush, or at the same elevation as each brush. In other embodiments, the one or more second fluid apertures 138 may be positioned anywhere on the shaft 128.

Figure 3B:
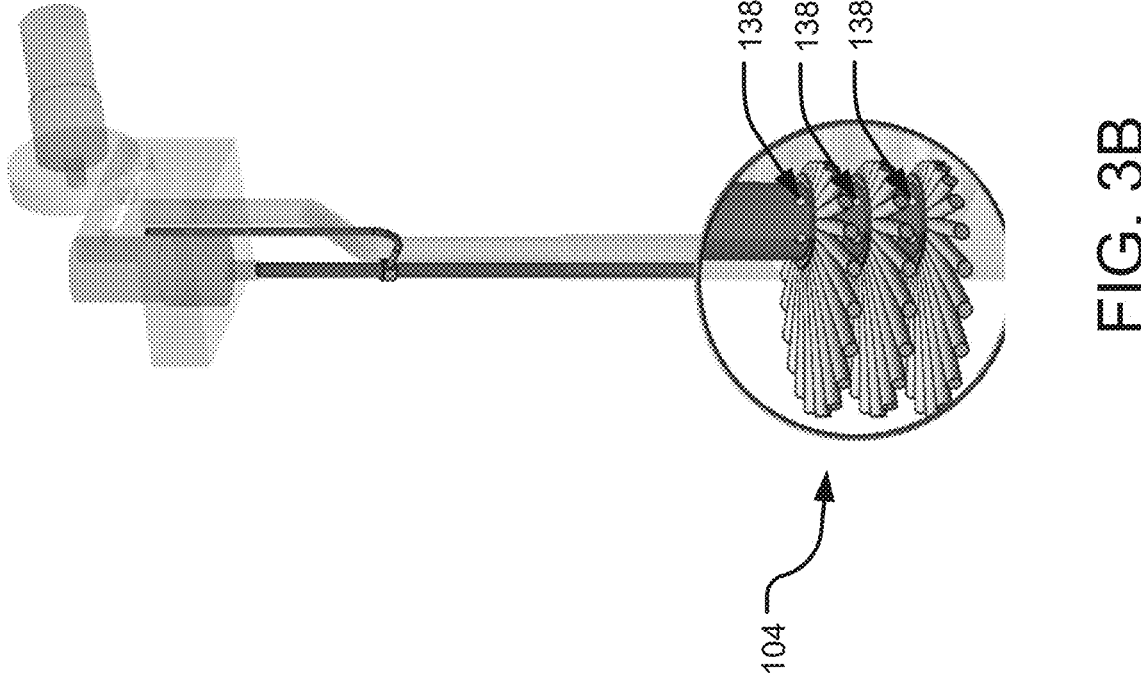
FIG. 3B depicts the tool of FIG. 1A according to at least one embodiment of the present disclosure, with another portion thereof shown in a close-up view.
Figure 3A:
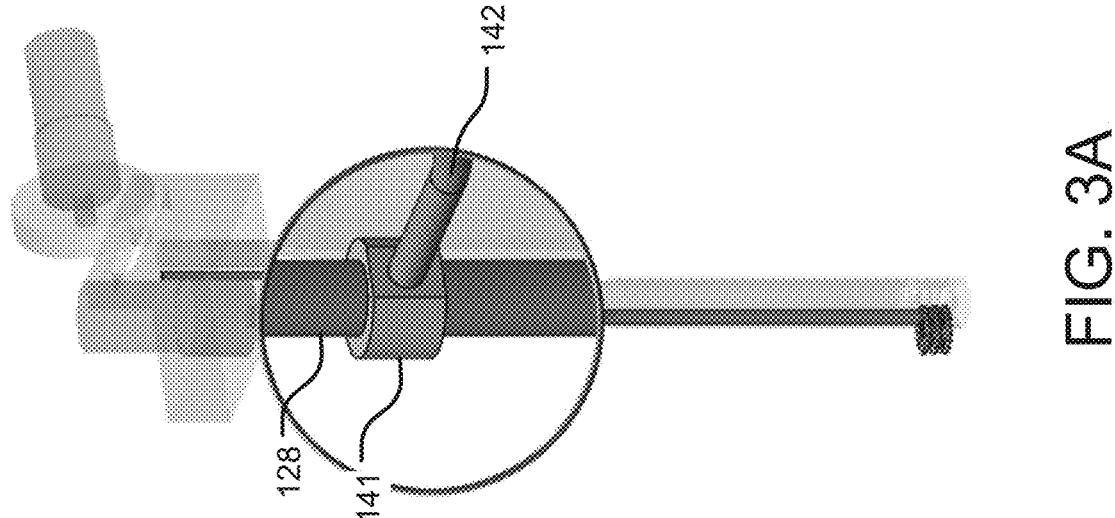
FIG. 3A depicts the tool of FIG. 1A according to at least one embodiment of the present disclosure, with a portion thereof shown in a close-up view.

FIGS. 3A and 3B illustrate further details of the tool 100 for supplying fluid to the brush set 104. Fluid is supplied to the one or more first fluid apertures 140 via a fluid tube 142 and a fluid ring 141. The ring 141 advantageously supplies fluid to the shaft 128 while also allowing the shaft 128 to rotate within the ring 141. As illustrated and described above, the second fluid apertures 138 are positioned on a proximate side and a distal side of each brush of the brush set 104 to enable fluid to be sprayed or otherwise discharged onto both side of each brush of the brush set 104. In some embodiments, the tube 102 may include one or more first fluid tube apertures corresponding to the one or more first fluid apertures 140 (e.g., in embodiments in which the tube 102 extends along a greater portion of the shaft 128, or where the fluid tube 142 and fluid ring 141 are positioned closer to the distal portion 112 of the tool 100) and one or more second fluid tube apertures corresponding to the one or more second fluid apertures 138.

Turning to FIGS. 4A-4C, the brush set 104 is shown moving from a closed position to a cleaning position during use. The brush set 104 may be continuously rotated (e.g., by continuous rotation of the shaft 128) between the cleaning position and the closed position to clean an anatomical element by alternately brushing the anatomical element (when in the cleaning position) and being cleaned of anatomical particles through a combination of fluid spray and suction (when in the closed position). As previously described, the brush set 104 is positioned inside of the tube 102 when in the closed position, as shown in FIG. 4A. In other words, the brush set 104 is positioned entirely within a perimeter of the tube 102 when in the closed position, in which position the brush set 104 can advantageously be cleaned by discharge of fluid from the second fluid apertures

138 thereon and by suction within the second or suction conduit 116. As the brush set 104 moves towards the cleaning position, as shown in FIGS. 4A and 4B (the cleaning position is shown, for example, in FIGS. 4C-4F), the brush set 104 rotates through the brush slot set 122 and out of the tube 102. As the brush set 104 rotates out of the tube 102 and through a complete rotation, the brush set 104 scrapes or brushes anatomical particles from the anatomical element to clean the surface of the anatomical element from anatomical particles (e.g., from a disc being removed).

When the brush set 104 moves from the cleaning position back to the closed position to complete a full rotation, as shown in FIG. 4F, the brush set 104 moves through the brush slot set 122. Whether throughout the rotation or only as the brush set 104 rotates through the closed position, fluid may also be supplied to the brush set 104 (e.g., via the second fluid apertures 138) to loosen and/or dislodge anatomical particles that may be stuck to the brush set 104 and/or prevent loose anatomical particles from becoming lodged in or stuck to the brush set 104. In some embodiments, the tube 102 blocks the second fluid apertures 138 when the brush set 104 is not in or close to the closed position, thus beneficially preventing fluid from being sprayed or discharged into the interbody space being cleaned. Further, as the brush set 104 moves through the brush slot set 122, the loose anatomical particles that may be stuck to each brush of the brush set 104 may be pushed off each brush when the loose anatomical particles contact an edge of the corresponding brush slot of the brush slot set 122 or the tube 102.

As shown and previously described, one or more evacuation slots 126 are disposed near the brush slot set 122 and in communication with the second conduit 116, also referred to as a suction conduit. The vacuum source 522 creates a suction in the second conduit 116 or the suction conduit, and as the loose anatomical particles are dislodged, the suction draws the loose anatomical particles (and surrounding fluid) through the evacuation slots 126 and through the second conduit 116 or suction conduit.

In the illustrated embodiment and as previously described, a first evacuation slot 126 may be disposed above the brush slot set 122 (e.g., on a proximal side of the brush slot set 122) and a second evacuation slot 126 may be disposed below the brush slot set 122 (e.g., on a distal side of the brush slot set 122). Inclusion of two evacuation slots 126 beneficially facilitates evacuation of loose anatomical particles and fluid from the interbody space. Moreover, when the tool 100 is moved upwards or away from the anatomical element, loose anatomical particles (and surrounding fluid) may be evacuated more readily through the second evacuation slot 126 and when the tool 100 is moved downwards or towards the anatomical element, loose anatomical particles (and surrounding fluid) may be evacuated more readily through the first evacuation slot 126. Also, as shown in the illustrated embodiment, the second conduit 116 or suction conduit is connected to a vacuum tube 144, shown in FIGS. 1A and 1B, through which the loose anatomical particles are suctioned. Though not shown, the vacuum tube 144 may be connected to a receptacle or waste disposal to receive and/or dispose of the loose anatomical particles and/or fluid.

Each of the various components of the tool 100 may be made of a metal, a metal alloy, a plastic, a composite, any other suitable material that enables the component to achieve the purpose thereof as described herein, and/or any combination of the foregoing. In some embodiments, one or more components of the tool 100 may be made of a radiolucent material, such as polyetheretherketone (PEEK)

or thermoplastic resins with carbon-fiber reinforcement. In other embodiments, none of the components of the tool 100 are radiolucent. The material(s) from which the various components of the tool 100 are made may be selected to enable the tool 100 and/or one or more portions thereof to be cleanable, sterilizable (whether by heat, chemical treatment, or otherwise), and/or reusable. Additionally and/or alternatively, the material(s) from which the various components of the tool 100 are made may be selected for ease of cleaning, replaceability, or repair.

A tool 100, as described above with respect to FIGS. 1-4F, may be used in a system 500, as shown in FIG. 5, though it will be understood that the tool 100 may be used independently of the system 500. The system 500 includes a computing device 502, a robot 504 (which may include or be holding the tool 100), a fluid source 520, a vacuum source 522, and/or a navigation system 506. In some embodiments of the present disclosure, systems such as the system 500 of FIG. 5 may not include one or more of the illustrated components, may include other components not shown in FIG. 5, and/or may include components similar to, but not the same as, one or more components of the system 500 shown in FIG. 5. For example, in some embodiments, the system 500 may not include the navigation system 506. In other embodiments, the system 500 may not include the fluid source 520 and/or the vacuum source 522.

The computing device 502 according to embodiments of the present disclosure may comprise a processor 508, a memory 510, a communication interface 512, and the user interface 514. A computing device such as the computing device 502 in some embodiments may have more components or fewer components than the computing device 502 shown in FIG. 5.

The processor 508 of the computing device 502 may be any processor described herein or any similar processor. The processor 508 may be configured to execute instructions stored in the memory 510, which instructions may cause the processor 508 to carry out one or more computing steps utilizing or based on data received from the user interface 514; one or more sensors included in, attached to, or otherwise monitoring operation of the tool 100; the computing device 502, and/or the navigation system 506.

The memory 510 may be or comprise RAM, DRAM, SDRAM, other solid-state memory, any memory described herein, or any other tangible, non-transitory memory for storing computer-readable data and/or instructions. The memory 510 may store information or data useful for completing any step of the method 600 described herein. The memory 510 may store, for example, one or more instructions 516 and/or one or more surgical plans 518. Such instructions 516 may, in some embodiments, be organized into one or more applications, modules, packages, layers, or engines. The instructions 516 may be configured for execution by the processor 508 to carry out any method described herein (including the method 600) or portion thereof, and/or to operate one or more of the robot 504, the navigation system 506, the tool 100, the fluid source 520, and/or the vacuum source 522. The instructions 516 may cause the processor 508 to manipulate data stored in the memory 510 and/or received from the navigation system 506.

The computing device 502 may also comprise a communication interface 512. The communication interface 512 may be used for receiving information from an external source (such as the tool 100, the robot 504, and/or the navigation system 506), and/or for transmitting instructions, data, or other information to an external system or device (e.g., the tool 100, the robot 504, and/or the navigation system 506). The communication interface 512 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, NFC, ZigBee, and so forth). In some embodiments, the communication interface 512 may be useful for enabling the computing device 502 to communicate with one or more other processors 508 or computing devices 502, whether to reduce the time needed to accomplish a computing-intensive task or for any other reason.

The computing device 502 may also comprise one or more user interfaces 514. The user interface 514 may be or comprise a keyboard, mouse, trackball, monitor, television, touchscreen, joystick, switch, button, headset and/or any other device for receiving information from a user and/or for providing information to a user. The user interface 514 may be used, for example, to receive a user selection or other user input regarding controlling a robot to position the tool 100 within an interbody space; a user selection or other user input regarding causing the brush set 104 to rotate between a cleaning position and a closed position in an alternating fashion; a user selection or other user input regarding causing a fluid source to supply a fluid to the brush set 104; a user selection or other user input regarding evacuating fluid from the brush set 104 through the suction conduit 116; a user selection or other user input regarding adjusting an elevation of the distal portion 112 of the tool 100; to receive user input useful in connection with the instructions 516 and/or the surgical plan 518, to receive a user selection or other user input regarding operation of the robot 504, manipulation of the robotic arm 524, and/or use of the tool 100; and/or to display the instructions 516 and/or the surgical plan 518. In some embodiments, the user interface 514 may be useful to allow a surgeon or other user to modify the instructions 516, the plan 518, or other information displayed, though it will be appreciated that each of the preceding inputs may be generated automatically by the system 500 (e.g., by the processor 508 or another component of the system 500) or received by the system 500 from a source external to the system 500. In some embodiments, user input such as that described above may be optional or not needed for operation of the systems, devices, and methods described herein.

Although the user interface 514 is shown as part of the computing device 502, in some embodiments, the computing device 502 may utilize a user interface 514 that is housed separately from one or more remaining components of the computing device 502. In some embodiments, the user interface 514 may be located proximate one or more other components of the computing device 502, while in other embodiments, the user interface 514 may be located remotely from one or more other components of the computing device 502.

The robot 504 may be any surgical robot or surgical robotic system. The robot 504 may be or comprise, for example, the Mazor X™ Stealth Edition robotic guidance system. The robot 504 may comprise one or more robotic arms 524. In some embodiments, the robotic arm 524 may comprise one robotic arm, though in other embodiments, the robotic arm 524 may comprise two robotic arms or more than two robotic arms. The tool 100 may be disposed on an end of the robotic arm 524. In other examples, the tool 100 may be disposed on any portion of the robotic arm 524 and/or the robot 504.

In some embodiments, the system 500 may include a navigation system 506, though in other embodiments, the system 500 may not include a navigation system 506. The navigation system 506 may provide navigation for a surgeon and/or a surgical robot during an operation. The navigation system 506 may be any now-known or future-developed navigation system, including, for example, the Medtronic StealthStation™ S8 surgical navigation system. In various embodiments, the navigation system 506 may be used to track a position of the robotic arm 524 (or, more particularly, of a navigated tracker attached to the robotic arm 524). The navigation system 506 may include a camera or other sensor(s) for tracking one or more reference markers, navigated trackers, or other objects within the operating room. The navigation system 506 may include a display for displaying one or more images from an external source (e.g., a camera or other source) or a video stream from the camera or other sensor of the navigation system 506. In some embodiments, the navigation system 506 may provide position, movement, and/or other information to the robot 504 for use in controlling the tool 100 and/or any other aspect of the system 500. In some embodiments, the system 500 does not include and can operate without the use of the navigation system 506.

Reference markers (i.e., navigation markers) may be placed on the robot 504, the robotic arm 524, the tool 100, or any other object in the surgical space. The reference markers may be tracked by the navigation system 506, and the results of the tracking may be used by the computing device 502 and/or by an operator of the system 500 or any component thereof. In some embodiments, the navigation system 506 can be used to track other components of the system (e.g., the tool 100) and the system 500 can operate without the use of the robot 504 (e.g., with the surgeon manually manipulating the tool 100).

The system 500 may also include the fluid source 520 and/or the vacuum source 522. In some embodiments, the system 500 does not include the fluid source 520 and/or the vacuum source 522, may include only the fluid source 520, or may include only the vacuum source 522. In other embodiments, the fluid source 520 and/or the vacuum source 522 may be used with the tool 100 independently of the system 500. Each of the fluid source 520 and/or the vacuum source 522 may be formed as a part of the tool 100 or may be separate from the tool 100. A hose (not shown) may extend from each of the fluid source 520 and the vacuum source 522 to the fluid tube 142 and the vacuum tube 144, respectively. The fluid source 520 may be configured to provide fluid to the brush set 104. The fluid may be a gas (e.g., oxygen, air, carbon dioxide, heliox) or a liquid (e.g., water, saline, or another irrigant). The fluid may flush loose anatomical particles from the brush set 104, and/or anatomical element. The fluid source 520 may be configured with a pressurized fluid storage container or may otherwise comprise a pressurized fluid source so as to enable the fluid to be discharged onto the brush set 104 under pressure. In such embodiments, the pressure may be selectable (whether by a surgeon or other human operator of the tool 100, or by the computing device 502, or otherwise). The vacuum source 522 may remove the fluid when used with the fluid source 520 and/or may remove loose anatomical particles when used with or without the fluid source 520. The fluid may be delivered to the anatomical element via the fluid tube 142 and the shaft 128, and/or removed from the anatomical element via the vacuum tube 144. In other embodiments, the fluid may be delivered to or removed from the anatomical element through or via any cannula, annulus, or hose formed on, disposed on, or connected to the tool 100.

Turning now to FIG. 6, a method 600 for performing a surgical procedure may be executed in whole or in part by a robot (e.g., the robot 504 controlled by the computing device 502) and/or a surgeon. The method 600 may be performed using, for example, the tool 100 described above with respect to FIGS. 1A-4C and/or the system 500 described above with respect to FIG. 5.

The method 600 comprises controlling a robot, such as the robot 504, to position a cleaning tool, such as the tool 100, within an interbody space (step 602). The cleaning tool may be attached to a robotic arm such as the robotic arm 524. The controlling may include sending instructions to the robot for manipulating the robotic arm to insert the cleaning tool into an interbody space, and may be based on, for example, a surgical plan such as a surgical plan 518, one or more images of the anatomy of the patient into which the cleaning tool is being inserted, user input, and/or other information. The instructions may include a predetermined position and orientation of the cleaning tool. The controlling may include providing a trajectory or movement path from the surgical plan to the robot, or determining, with a processor such as the processor 508, a trajectory or movement path for the robot that will result in the cleaning tool being properly positioned within the interbody space, and then providing the determined trajectory or movement path to the robot. In some instances, the tool may be used manually by a surgeon, which surgeon may in some embodiments be assisted by the robot and/or a navigation system (e.g., the navigation system 506).

The method 600 also comprises causing a brush set (e.g., the brush set 104) of the tool to rotate between a cleaning position and a closed position in alternating fashion (step 604). As described with respect to FIGS. 2B and 4A-4C, the brush set is positioned entirely within a perimeter of a tube (e.g., the tube 102) of the tool when in the closed position. The tube may have a corresponding brush slot of a brush slot set through which each brush passes on each rotation. The brush set may dislodge or remove anatomical particles from an anatomical element to clean a surface of the anatomical element.

The method 600 also comprises causing a fluid source (e.g., the fluid source 520) of the tool to supply a fluid to the brush set (step 606). As previously described with respect to FIGS. 2A-3B, the fluid is supplied to each brush of the brush set as each brush rotates through the closed position. In some embodiments, the fluid is constantly supplied to the brush set. The fluid may prevent loose anatomical particles from sticking to the brush set and/or may loosen anatomical particles lodged in the brush set.

The method 600 further comprises causing the fluid (and any anatomical particles entrained therein) to be evacuated from the brush set though a suction conduit (e.g., the second conduit 116) of the tool (step 608). As previously described with respect to FIGS. 1A-1B, the fluid and/or loose anatomical particles may be evacuated from the site through an evacuation slot disposed near the brush slot set. The evacuating may not result in complete removal of all of the fluid provided in the step 606. Further, loose anatomical particles may be dislodged as the brush set passes through the corresponding brush slot set to the closed position and the loose particles may be evacuated through the evacuation slot and the suction conduit. Rotation of the brush set between the cleaning position and the closed position may be continuously repeated until the surface of the anatomical element is sufficiently cleaned.

The method 600 further comprises causing an adjustment of an elevation of a distal portion, such as the distal portion 112, of the cleaning tool (step 610). The elevation of the cleaning tool may be adjusted via an elevation motor, such as the elevation motor 108. The elevation may be continuously adjusted or adjusted in discrete increments autonomously or under direction of the surgeon. By continuously adjusting the elevation of the distal portion, an elevation of the brush set is continuously adjusted during use to form a vibration motion, thereby facilitating thorough cleaning of the interbody space.

In some embodiments, the method 600 may comprise receiving the surgical plan (e.g., the surgical plan 518). The surgical plan may be received via a user interface such as the user interface 514 and/or a communication interface such as the communication interface 512 of a computing device such as the computing device 502, and may be stored in a memory such as the memory 510 of the computing device. The surgical plan may include information about one or more planned movements of the tool (and/or of the robot holding the tool) during a surgical procedure. The information may also include a timeline or schedule of the one or more planned movements. The one or more planned movements may include one or more of timestamps, a type of movement (e.g., translational and/or rotational), a duration of the movement, and/or positional information (e.g., coordinates).

In some embodiments, the method 600 may comprise determining information about one or more needed movements of the tool during a surgical procedure outlined or otherwise described in a surgical plan. In such embodiments, the surgical plan may not include receiving any such information via the computing device, but through the processor executing instructions stored in the memory, which may generate such information based on the surgical plan.

In some embodiments, the method 600 may comprise generating instructions such as the instructions 516 for causing the tool (e.g., the tool 100) to perform one or more surgical steps such as those described in connection with the steps 602 to 610. The instructions may be based on the surgical plan. In some embodiments, however, the tool may be automatically actuated based on instructions stored in a memory thereof that are not based on a surgical plan.

The instructions 516 may include one or more instructions that cause an alert or other indication to be given to the surgeon (e.g., via a user interface such as the user interface 514) prior to each movement of the tool, and/or prior to executing one of the one or more planned surgical steps. In some embodiments, such an alert may pause execution of the surgical plan for approval by the surgeon or other operator. In other embodiments, the alert may simply notify the surgeon of the planned movement and/or of the planned volume increase or decrease, and automatically execute the planned movement. The alert and/or notification may be displayed on the user interface and/or may include a sound and/or a visual display.

As may be appreciated based on the foregoing disclosure, the present disclosure encompasses methods with fewer than all of the steps identified in FIG. 6 (and the corresponding description of method 600), as well as methods that include additional or other steps beyond those identified in FIG. 6 (and the corresponding description of method 600).

The methods and systems described herein provide a tool that can prepare a surface of an anatomical element for a fusion or other surgical procedure. The tool is self-cleaning and may be reusable, thereby eliminating the need for a surgeon or surgical robot to switch brushes during cleaning and resulting in reduced operating time and less trauma to the neutral tissue of the patient along the insertion/removal path. Further, a lack of switching brushes or tools reduces potential risk of accidental impact from a tool or brush being removed or inserted into the surgical site. The brush is also protected during positioning, thereby reducing risk of damage to the brush prior to cleaning of the anatomical element.

The foregoing discussion has been presented for purposes of illustration and description. The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A surgical tool, comprising:
a tube with a proximal end, a distal end, and at least one brush slot positioned between the proximal end and the distal end and extending at least partially around a circumference of the tube;
at least one brush disposed on a shaft extending through the tube;
a motor operable to rotate the shaft about a shaft axis to cause the at least one brush to move between a closed position and a cleaning position, wherein the at least one brush is positioned entirely inside of the tube when in the closed position, and wherein the at least one brush extends radially outward from the tube through the at least one brush slot when in the cleaning position; and
a fluid source operable to supply fluid to the at least one brush as the at least one brush passes through the at least one brush slot,
wherein the at least one brush has a brush axis that passes through a center of the at least one brush, and wherein the brush axis is parallel to and offset from the shaft axis of the shaft.

2. The surgical tool of claim 1, wherein the fluid is supplied through a conduit of the shaft.

3. The surgical tool of claim 1, wherein the tube comprises a first conduit and a second conduit parallel to the first conduit, wherein the shaft extends through the first conduit, and wherein each of the brush axis and the shaft axis are parallel to and offset from an axis of the second conduit.

4. The surgical tool of claim 1, further comprising a suction conduit for evacuating the fluid.

5. The surgical tool of claim 4, further comprising at least one evacuation slot disposed distal to or proximal to the at least one brush slot, wherein the at least one evacuation slot is in fluid communication with the suction conduit.

6. The surgical tool of claim 5, wherein, as the at least one brush passes through the at least one brush slot when moving from the cleaning position to the closed position, the at least one evacuation slot evacuates the fluid from the at least one brush.

7. The surgical tool of claim 1, wherein the at least one brush comprises a plurality of steel bristles of varying lengths.

8. The surgical tool of claim 7, wherein the plurality of steel bristles forms a circle.

9. The surgical tool of claim 1, wherein the at least one brush comprises three brushes.

10. The surgical tool of claim 9, further comprising an elevation motor configured to translate the surgical tool during operation of the surgical tool.

11. The surgical tool of claim 1, wherein the at least one brush defines an essentially circular shape in the closed position and in the cleaning position.

12. A system for cleaning an anatomical space, comprising:
   a surgical tool comprising:
      a tube with a proximal end, a distal end, and a plurality of brush slots each positioned between the proximal end and the distal end, wherein each slot of the plurality of brush slots extends at least partially around a circumference of the tube;
      a plurality of brushes disposed on a shaft that extends through the tube, wherein each brush of the plurality of brushes corresponds to and aligns with a slot of the plurality of brush slots; and
      a fluid source;
   a processor; and
   a memory storing instructions for execution by the processor that, when executed, cause the processor to:
      rotate the shaft about a shaft axis to cause the plurality of brushes of the surgical tool to rotate between a cleaning position and a closed position, wherein each brush of the plurality of brushes extends radially outward from the tube through the corresponding brush slot to contact an anatomical element when in the cleaning position, wherein the plurality of brushes are aligned along a brush axis that passes through a center of each brush of the plurality of brushes, and wherein the brush axis is parallel to and offset from the shaft axis of the shaft;

cause the fluid source to supply a fluid to the plurality of brushes when moving from the cleaning position to the closed position; and
evacuate the fluid and loose anatomical elements from the plurality of brushes.

13. The system of claim 12, wherein each brush of the plurality of brushes comprises a plurality of steel bristles of varying lengths.

14. The system of claim 12, wherein the instructions for execution by the processor, when executed, further cause the processor to cause a motor to translate the surgical tool during operation of the surgical tool.

15. The system of claim 12, wherein rotation of the shaft causes the brush axis to orbit around the shaft axis.

16. The system of claim 12, wherein the plurality of brushes comprises three brushes.

17. A method for brushing an anatomical element, comprising:
   causing a plurality of brushes of a surgical tool to alternately rotate between a cleaning position and a closed position, wherein the plurality of brushes is disposed on a shaft and is positioned entirely within a perimeter of a tube of the surgical tool when in the closed position, wherein the tube has a proximal end, a distal end, and a plurality of slots each positioned between the proximal end and the distal end, wherein each slot corresponds to and aligns with a brush of the plurality of brushes, wherein each brush of the plurality of brushes extends radially outward from the tube through the corresponding brush slot when in the cleaning position, wherein the shaft has a shaft axis and the plurality of brushes is aligned along a brush axis that passes through a center of each brush of the plurality of brushes, and wherein the brush axis is parallel to and offset from the shaft axis;
   causing a fluid source of the surgical tool to supply a fluid to the plurality of brushes from the fluid source as the plurality of brushes rotates through the closed position; and
   evacuating the fluid from the plurality of brushes through a suction conduit of the surgical tool, the suction conduit in fluid communication with an evacuation slot disposed distal to or proximal to the plurality of slots.

18. The method of claim 17, wherein the shaft comprises a bore and at least one fluid aperture positioned proximal to or distal to the plurality of brushes, and wherein the fluid is supplied to the plurality of brushes through the bore and the at least one fluid aperture.

19. The method of claim 17, further comprising:
   translating the surgical tool using a motor during operation of the surgical tool.

20. The method of claim 17, wherein the plurality of brushes comprises a plurality of steel bristles of varying lengths.

* * * * *